US008445405B2

(12) United States Patent
Rodriguez Contreras et al.

(10) Patent No.: US 8,445,405 B2
(45) Date of Patent: May 21, 2013

(54) SYNERGISTIC HERBICIDAL COMPOSITIONS CONTAINING AMINOPYRALID, 2,4-DICHLOROPHENOXYACETIC ACID AND ATRAZINE

(75) Inventors: Sergio Rodriguez Contreras, Zapopan (MX); Carlos E. Rojas-Calvo, Guadalajara (MX); Robert A. Masters, Zionsville, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/181,620

(22) Filed: Jul. 13, 2011

(65) Prior Publication Data

US 2012/0015808 A1 Jan. 19, 2012

Related U.S. Application Data

(60) Provisional application No. 61/364,099, filed on Jul. 14, 2010.

(51) Int. Cl.
*A01N 43/64* (2006.01)

(52) U.S. Cl.
USPC .......................................................... 504/134

(58) Field of Classification Search
None
See application file for complete search history.

(56) References Cited

U.S. PATENT DOCUMENTS

2008/0242546 A1* 10/2008 Schultz et al. ................ 504/130

FOREIGN PATENT DOCUMENTS

RO 106 494 B1 5/1993
WO WO 2012/009395 1/2012

OTHER PUBLICATIONS

J.W. Ludwig: "The Use of a Low Dose of Atrazine Alone and in Mixtures With Other Herbicides in the Maize Crop", Weed Research, vol. 13, Jan. 1, 1973, pp. 12-18.*

Walker et al: "Effect of herbicides on black pigweed and sesbania pea, and yields of five grain sorghum cultivars in central Queensland", Jan. 1, 1988, Australian Journal of Experimental Agriculture, Csiro, Collingwod, AU, p. 327-332, XP009154867, ISSN: 0816-1089 and Schultz et al., US20080242546; Oct. 2, 2008.*

RO 106 494 B1 (SC Chimcomplex SA Borzesti One [RO]) May 31, 1993.*

J.W. Ludwig: "The Use of a Low Dose of Atrazine Alone and in Mixtures with Other Herbicides in the Maize Crop", Weed Research, col. 13, Jan. 1, 1973, pp. 12-18.

Walker S R, et al.: "Effect of herbicides on black pigweed and sesbania pea, and yields of five grain sorghum cultivars in central Queensland", Jan. 1, 1988, Australian Journal of Experimental Agriculture, CSIRO, Collingwood, AU, pp. 327-332.

* cited by examiner

*Primary Examiner* — Alton Pryor
(74) *Attorney, Agent, or Firm* — Robert Chang

(57) ABSTRACT

An herbicidal composition containing (a) aminopyralid and 2,4-D and (b) atrazine provides synergistic control of selected weeds in corn, sorghum, sugar cane and range and pasture.

16 Claims, No Drawings

SYNERGISTIC HERBICIDAL COMPOSITIONS CONTAINING AMINOPYRALID, 2,4-DICHLOROPHENOXYACETIC ACID AND ATRAZINE

CROSS REFERENCE TO RELATED APPLICATIONS

This application claims the benefit of U.S. Provisional Patent Application Ser. No. 61/364,099 filed Jul. 14, 2010.

FIELD OF THE INVENTION

This invention concerns a synergistic herbicidal composition containing (a) aminopyralid and 2,4-dichlorophenoxyacetic acid (2,4-D) and (b) atrazine.

BACKGROUND OF THE INVENTION

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use.

In some cases, herbicidal active ingredients have been shown to be more effective in combination than when applied individually and this is referred to as "synergism." As described in the *Herbicide Handbook* of the Weed Science Society of America, Ninth Edition, 2007, p. 429, "'synergism' [is] an interaction of two or more factors such that the effect when combined is greater than the predicted effect based on the response to each factor applied separately." The present invention is based on the discovery that (a) aminopyralid and 2,4-D and (b) atrazine, already known individually for their herbicidal efficacy, display a synergistic effect when applied in combination.

The herbicidal compounds forming the synergistic composition of this invention are independently known in the art for their effects on plant growth.

Aminopyralid, 4-amino-3,6-dichloro-2-pyridinecarboxylic acid, is a picolinic acid or pyridine herbicide. It is described in *The Pesticide Manual,* Fifteenth Edition, 2009. Aminopyralid is used for long-term control of annual and perennial broadleaf weeds in grassland.

2,4-D is the common name for 2,4-dichlorophenoxyacetic acid. Its herbicidal activity is described in *The Pesticide Manual,* Fifteenth Edition, 2009. 2,4-D controls both annual and perennial broadleaf weeds in a variety of grassy crops.

Atrazine is the common name for 6-chloro-N-ethyl-N'-(1-methylethyl)-1,3,5-triazine-2,4-diamine. Its herbicidal activity is described in *The Pesticide Manual,* Fifteenth Edition, 2009. Atrazine provides pre- and post-emergence control of annual broadleaf weeds and annual grasses in maize, sorghum, sugar cane, pineapples, chemical fallow, grassland, macadamia nuts, conifers, and industrial weed control.

Tronador™ herbicide is a post-emergence herbicide containing aminopyralid at 9 grams acid equivalent per liter (g ae/L) and 2,4-D at 180 g ae/L in a soluble concentrated formulation, sold by Dow AgroSciences LLC. Tronador™ herbicide controls several broadleaf weeds in corn crops. Tronador at 1.5 L/ha is equivalent to 283.5 g ae/ha (13.5 g ae/ha aminopyralid +270 g ae/ha 2,4-D).

SUMMARY OF THE INVENTION

The present invention concerns a synergistic herbicidal mixture comprising an herbicidally effective amount of (a) aminopyralid and 2,4-D and (b) atrazine. The compositions may also contain an agriculturally acceptable adjuvant or carrier.

The present invention also concerns a method of controlling undesirable vegetation, particularly in corn, sorghum, sugar cane and range and pastures, which comprises contacting the vegetation or the locus thereof with an herbicidally effective amount of the herbicidal mixture provided herein.

The species spectrum of the compounds of the synergistic mixture, i.e., the weed species which the respective compounds control, are broad and highly complementary.

These synergistic mixtures are particularly useful for the control of key weeds, e.g., bur-cucumber (*Sicyos angulatus* L.; SIYAN) at application rates lower than the rates of the individual compounds.

DETAILED DESCRIPTION OF THE INVENTION

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings and established vegetation.

Herbicidal activity is exhibited by the compounds of the synergistic mixture when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the synergistic mixture of the present invention post-emergence to relatively immature undesirable vegetation to achieve the maximum control of weeds.

In the composition of this invention, the weight ratio of aminopyralid to 2,4-D lies within the range of between about 1:15 and about 1:25 on an acid equivalent basis. Preferably the weight ratio of aminopyralid to 2,4-D is about 1:20 on an acid equivalent basis. The rate of Tronador™ herbicide applied will range from about 141 to about 378 g ae/ha. The weight ratio of aminopyralid (acid equivalent) to atrazine (active ingredient) at which the herbicidal effect is synergistic lies within the range of about 1:25 and about 1:100.

The rate at which atrazine is applied will range from about 400 to about 1000 grams active ingredient per hectare (g ai/ha).

The rate at which the synergistic composition is applied will depend upon the particular type of weed to be controlled, the degree of control required, and the timing and method of application. In especially preferred embodiments of the invention, Tronador™ herbicide is applied at a rate of 283.5 g ae/ha, and atrazine is applied at a rate between about 450 g ai/ha and about 900 g ai/ha.

The components of the synergistic mixture of the present invention can be applied either separately or as part of a multipart herbicidal system.

The synergistic mixture of the present invention can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the synergistic composition of the present invention include: acetochlor, alachlor, ametryn, amicarbazone, amidosulfuron, aminocyclopyrachlor, asulam, benfuresate, bentazone, bromoxynil, butafenacil, chlorsulfuron, clomazone, clopyralid, cyanazine, dicamba, diflufenzopyr, dimethenamid, dimethenamid-p, diquat, diuron, flazasulfuron, flumetsulam, flumioxazin, fluroxypyr, foramsulfuron, glyphosate, halosulfuron, hexazinone, imazapic, imazamox, imazapyr, imazethapyr, iodosulfuron, linuron, MCPA, MCPB, metolachlor, metribuzin, metsulfuron methyl, MSMA, nicosulfuron, paraquat, pendimethalin, penoxsulam, picloram, propachlor, prosulfuron, pyroxasulfone, quinclorac, rimsulfuron, simazine, s-metolachlor, sulcotrione, sulfosulfuron, sulfomethuron, tebuthiuron, terbuthylazin, thifensulfuron, triclopyr ester, triclopyr triethylamine and 5-hydroxypyrazoles.

The composition of the present invention can additionally be employed to control undesirable vegetation in many crops that have been made tolerant to or resistant to them or to other herbicides by genetic manipulation or by mutation and selection. Thus, the composition of the present invention can be used on 2,4-D tolerant crops. The herbicidal composition of the present invention can, further, be used in conjunction with glyphosate, glufosinate, dicamba or imidazolinones on glyphosate-tolerant, glufosinate-tolerant, dicamba-tolerant or imidazolinone-tolerant crops. It is generally preferred to use the composition of the invention in combination with herbicides that are selective for the crop being treated and which complement the spectrum of weeds controlled by these compounds at the application rate employed. It is further generally preferred to apply the composition of the invention and other complementary herbicides at the same time, either as a combination formulation or as a tank mix. Similarly the herbicidal composition of the present invention can be used in conjunction with acetolactate synthase inhibitors on acetolactate synthase inhibitor-tolerant crops.

The synergistic composition of the present invention can generally be employed in combination with known herbicide safeners, such as benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, mefenpyr-diethyl, MG 191, MON 4660, naphthalic anhydride (NA), oxabetrinil, R29148 and N-phenylsulfonylbenzoic acid amides, to enhance their selectivity.

While it is possible to utilize the synergistic mixture of the present invention directly as herbicides, it is preferable to use them in mixtures containing an herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of the synergistic mixture or other composition ingredients. Such mixtures can be designed for application directly to weeds or their locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions. They can also be provided as a pre-mix or tank mixed.

Suitable agricultural adjuvants and carriers that are useful in preparing the herbicidal mixtures of the invention are well known to those skilled in the art. Some of these adjuvants include, but are not limited to, crop oil concentrate (mineral oil (85%) +emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water and organic solvents. The organic solvents typically used include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., N.Y., 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, particularly methyl esters.

Oftentimes, some of these materials, such as vegetable or seed oils and their esters, can be used interchangeably as an agricultural adjuvant, as a liquid carrier or as a surface active agent.

Other additives commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like, and can be formulated with liquid fertilizers or solid, particulate fertilizer carriers such as ammonium nitrate, urea and the like.

The concentration of the active ingredients in the synergistic composition of the present invention is generally from 0.001 to 98 percent by weight. Concentrations from 10 to 90 percent by weight are often employed. In compositions designed to be employed as concentrates, the active ingredients are generally present in a concentration from 5 to 98 weight percent, preferably 10 to 90 weight percent. Such compositions are typically diluted with an inert carrier, such as water, before application. The diluted compositions usually applied to weeds or the locus of weeds generally contain 0.0001 to 1 weight percent active ingredient and preferably contain 0.001 to 0.1 weight percent.

The present compositions can be applied to weeds or their locus by the use of conventional ground or aerial dusters, sprayers, and granule applicators, by addition to irrigation water, and by other conventional means known to those skilled in the art.

EXAMPLES

Evaluation of Tronador™ herbicide and Atrazine Tank Mixes for Post Emergence Synergistic Weed Control in Corn in Mexico These trials were conducted under normal corn crop conditions. Trial sites were located in commercially grown corn in the Jalisco (Mexico) area. The corn crop was grown using normal cultural practices for fertilization, seeding, and maintenance to ensure good growth of the crop and the weeds. The trials were conducted using normal research methodology. Trial plots were between 6 to 7 meters (m) wide by 10 m long. All treatments were applied using a randomized complete block trial design with 3 or 4 replications per treatment. The trial sites had naturally occurring populations of weeds. The weed spectrum included, but was not limited to, redroot pigweed (*Amaranthus retroflexus,* AMARE), bur-cucumber (*Sicyos angulatus,* SIYAN). Treatments consisted of tank mixes of Tronador™ herbicide and atrazine applied in water. The application volumes were between 250 to 300 liters per hectare (L/ha). All applications were made using precision gas hand sprayers using a 3 m boom using flat fan 8002 nozzles to broadcast the treatments on the weeds.

The treated plots and control plots were rated blind at various intervals after application. Ratings were based on Percent (%) Visual weed control, where 0 corresponds to no injury and 100 corresponds to complete kill.

Colby's equation was used to determine the herbicidal effects expected from the mixtures (Colby, S. R. *Weeds* 1967, 15, 20-22. Calculation of the synergistic and antagonistic response of herbicide combinations).

The following equation was used to calculate the expected activity of mixtures containing two active ingredients, A and B:

$$\text{Expected}=A+B-(A\times B/100)$$

A=observed efficacy of active ingredient A at the same concentration as used in the mixture.

B=observed efficacy of active ingredient B at the same concentration as used in the mixture.

The herbicide tank mix combinations tested, application rates and ratios employed, plant species tested, and results are given in Table 1.

TABLE 1

Synergistic weed control following an application of Tronador ™ herbicide (aminopyralid 13.5 g ae/ha + 2,4-D 270 g ae/ha) and atrazine (450 and 900 g ai/ha) 15, 30, 45 and 60 days after application

| Tronador | Atrazine | SIYAN | | AMARE | |
|---|---|---|---|---|---|
| (g ae/ha) | (g ai/ha) | Obs | Exp | Obs | Exp |
| 15 DAYS AFTER APPLICATION | | | | | |
| 283.5 | — | 3 | — | 35 | — |
| — | 450 | 27.5 | — | 35 | — |
| — | 900 | 42.5 | — | 46.3 | — |
| 283.5 | 450 | 55 | 29.675 | 66.3 | 57.75 |
| 283.5 | 900 | 72.5 | 73.325 | 73.8 | 65.095 |
| 30 DAYS AFTER APPLICATION | | | | | |
| 283.5 | — | 3.3 | — | 88.8 | — |
| — | 450 | 36.3 | — | 77.5 | — |
| — | 900 | 60 | — | 82.5 | — |
| 283.5 | 450 | 90 | 38.4021 | 99 | 97.48 |
| 283.5 | 900 | 99 | 61.32 | 99 | 98.04 |
| 45 DAYS AFTER APPLICATION | | | | | |
| 283.5 | — | 3 | — | 99 | — |
| — | 450 | 56.3 | — | 91.3 | — |
| — | 900 | 66.3 | — | 94.8 | — |
| 283.5 | 450 | 95.8 | 57.611 | 99 | 99.913 |
| 283.5 | 900 | 99 | 67.311 | 99 | 99.948 |
| 60 DAYS AFTER APPLICATION | | | | | |
| 283.5 | — | 2.8 | — | 94.8 | — |
| — | 450 | 53.8 | — | 91.3 | — |
| — | 900 | 65 | — | 97 | — |
| 283.5 | 450 | 99 | 55.0936 | 99 | 99.5476 |
| 283.5 | 900 | 99 | 65.98 | 99 | 99.844 |

SIYAN - bur-cucumber (*Sicyos angulatus*)
AMARE - redroot pigweed (*Amaranthus retroflexus*)
g ae/ha - grams of acid equivalent per hectare
g ai/ha - grams of active ingredient per hectare
Obs - Percent control observed
Exp - Percent control expected by Colby equation

What is claimed is:

1. A synergistic herbicidal mixture comprising an herbicidally effective amount of (a) aminopyralid and 2,4-D and (b) atrazine.

2. The mixture of claim 1 in which the weight ratio of aminopyralid to 2,4-D is between about 1:15 and about 1:25 on an acid equivalent basis and the weight ratio of aminopyralid (acid equivalent) to atrazine (active ingredient) is between about 1:25 and about 1:100.

3. The mixture of claim 2 in which weight ratio of aminopyralid to 2,4-D is about 1:20 on an acid equivalent basis and the rate of aminopyralid and 2,4-D applied is from about 141 to about 378 g ae/ha and the rate of atrazine applied is from about 400 to 1000 g ai/ha.

4. The mixture of claim 2 in which weight ratio of aminopyralid to 2,4-D is about 1:20 on an acid equivalent basis and the rate of aminopyralid and 2,4-D applied is about 283.5 g ae/ha and the rate of atrazine applied is from about 450 to 900 g ai/ha.

5. An herbicidal composition comprising an herbicidally effective amount of the herbicidal mixture of claim 1 and an agriculturally acceptable adjuvant or carrier.

6. A method of controlling undesirable vegetation which comprises contacting the vegetation or the locus thereof with an herbicidally effective amount of the herbicidal mixture of claim 1.

7. A method of controlling undesirable vegetation in corn which comprises contacting the vegetation or the locus thereof with an herbicidally effective amount of the herbicidal mixture of claim 1.

8. The herbicidal composition of claim 5 in which the weight ratio of aminopyralid to 2,4-D is between about 1:15 and about 1:25 on an acid equivalent basis and the weight ratio of aminopyralid (acid equivalent) to atrazine (active ingredient) is between about 1:25 and about 1:100.

9. The herbicidal composition of claim 8 in which the weight ratio of aminopyralid to 2,4-D is about 1:20 on an acid equivalent basis and the rate of aminopyralid and 2,4-D applied is from about 141 to about 378 g ae/ha and the rate of atrazine applied is from about 400 to 1000 g ai/ha.

10. The herbicidal composition of claim 8 in which the weight ratio of aminopyralid to 2,4-D is about 1:20 on an acid equivalent basis and the rate of aminopyralid and 2,4-D applied is about 283.5 g ae/ha and the rate of atrazine applied is from about 450 to 900 g ai/ha.

11. The method of claim 6 in which the weight ratio of aminopyralid to 2,4-D is between about 1:15 and about 1:25 on an acid equivalent basis and the weight ratio of aminopyralid (acid equivalent) to atrazine (active ingredient) is between about 1:25 and about 1:100.

12. The method of claim 11 in which the weight ratio of aminopyralid to 2,4-D is about 1:20 on an acid equivalent basis and the rate of aminopyralid and 2,4-D applied is from about 141 to about 378 g ae/ha and the rate of atrazine applied is from about 400 to 1000 g ai/ha.

13. The method of claim 11 in which the weight ratio of aminopyralid to 2,4-D is about 1:20 on an acid equivalent basis and the rate of aminopyralid and 2,4-D applied is about 283.5 g ae/ha and the rate of atrazine applied is from about 450 to 900 g ai/ha.

14. The method of claim 7 in which the weight ratio of aminopyralid to 2,4-D is between about 1:15 and about 1:25 on an acid equivalent basis and the weight ratio of aminopyralid (acid equivalent) to atrazine (active ingredient) is between about 1:25 and about 1:100.

15. The method of claim 14 in which the weight ratio of aminopyralid to 2,4-D is about 1:20 on an acid equivalent basis and the rate of aminopyralid and 2,4-D applied is from about 141 to about 378 g ae/ha and the rate of atrazine applied is from about 400 to 1000 g ai/ha.

16. The method of claim 14 in which the weight ratio of aminopyralid to 2,4-D is about 1:20 on an acid equivalent basis and the rate of aminopyralid and 2,4-D applied is about 283.5 g ae/ha and the rate of atrazine applied is from about 450 to 900 g ai/ha.

* * * * *